(12) United States Patent
Jackson

(10) Patent No.: US 8,543,417 B1
(45) Date of Patent: Sep. 24, 2013

(54) SYSTEMS AND METHODS FOR DISPENSING AND COLLECTING DATA RELATED TO CONTROLLED SUBSTANCES

(76) Inventor: Delvin Ray Jackson, Cameron, MO (US)

( * ) Notice: Subject to any disclaimer, the term of this patent is extended or adjusted under 35 U.S.C. 154(b) by 369 days.

(21) Appl. No.: 12/638,095

(22) Filed: Dec. 15, 2009

Related U.S. Application Data

(60) Provisional application No. 61/122,426, filed on Dec. 15, 2008.

(51) Int. Cl.
*G06Q 50/00* (2012.01)

(52) U.S. Cl.
USPC .................................. 705/2; 705/3; 221/129

(58) Field of Classification Search
USPC ........................................ 705/2–3; 221/129
See application file for complete search history.

(56) References Cited

U.S. PATENT DOCUMENTS

| | | | | |
|---|---|---|---|---|
| 5,713,485 A * | 2/1998 | Liff et al. | ............................ | 221/2 |
| 5,832,449 A * | 11/1998 | Cunningham | ..................... | 705/3 |
| 6,345,260 B1 * | 2/2002 | Cummings et al. | ........... | 705/7.19 |
| 2002/0032582 A1 * | 3/2002 | Feeney et al. | ...................... | 705/2 |
| 2002/0055856 A1 * | 5/2002 | Adams | ................ | 705/2 |
| 2004/0254837 A1 * | 12/2004 | Roshkoff | ......................... | 705/14 |
| 2005/0060063 A1 * | 3/2005 | Reichelt et al. | ................ | 700/244 |
| 2005/0187790 A1 * | 8/2005 | Lapsker | ............................. | 705/2 |

* cited by examiner

*Primary Examiner* — Sind Phongsvirajati
(74) *Attorney, Agent, or Firm* — Lawrence Aaronson

(57) ABSTRACT

A system for providing pharmaceutical manufacturers marketing data related to the provision of samples includes an automated sample dispensing unit, a collateral materials printing device, a product information communication device, related prescription data flow information management services, companion wireless devices, robotic dispensing techniques, and bar code scanning capabilities.

19 Claims, 14 Drawing Sheets

Information Flows

Provider PDA/Computing Device

Rep PDA/Computing Device

Pharmacy

SYSTEMS AND METHODS FOR DISPENSING AND COLLECTING DATA RELATED TO CONTROLLED SUBSTANCES

CROSS-REFERENCE TO RELATED APPLICATION

The present application claims priority to U.S. Provisional Patent Application Ser. No. 61/122,426, entitled "Systems and Methods for Dispensing and Collecting Data Related to Controlled Substances", filed on Dec. 15, 2008, the contents of which are hereby incorporated by reference in their entirety.

BACKGROUND

Current estimates are that one third of all distributed samples of pharmaceutical products and other controlled substances are either wasted or expired and do not lead to new prescriptions. In addition, the current method of distribution is subject to frequent diversion, random allocation to patients, sporadic placement by field representatives, and excessive costs associated shipping and field base storage.

SUMMARY

A system for providing pharmaceutical manufacturers marketing data related to the provision of samples includes an automated sample dispensing unit, a collateral materials printing device, a product information communication device, related prescription data flow information management services, companion wireless devices, robotic dispensing techniques, and bar code scanning capabilities.

In accordance with some implementations, there is provided a system for dispensing controlled substances and collection data associated with the controlled substances. The system includes a dispensing unit housing the controlled substances in respective storage compartments; a data collection service that receives information associated with the controlled substances; and an application server that provides an interface to the information associated with the controlled substances. The dispensing unit may store, monitor and dispenses the controlled substances. The dispensing unit may also generate a prescription for a dispensed controlled substance.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative implementations, is better understood when read in conjunction with the appended drawings. For the purpose of illustrating the implementations, there are shown in the drawings example constructions of the implementations; however, the implementations are not limited to the specific methods and instrumentalities disclosed. In the drawings.

DETAILED DESCRIPTION

In implementations described below, a system for providing pharmaceutical manufacturers marketing data related to the provision of samples may include: an automated sample dispensing unit, a collateral materials printing device, a product information communication device, related prescription data flow information management services, companion wireless/computing devices, robotic dispensing techniques, and inventory management capabilities. The system and the related services address the challenges that the pharmaceutical industry and medical providers are facing who rely on professional samples for the treatment of their patient population. Implementations described herein, manage, distribute, and account for the samples being delivered to the medical community. The wireless/computing devices and dispensing technique described herein below, enables field representatives and pharmaceutical brand managers to be more responsive to provider sample demands, identify regional and local sample trends, gain competitive sample intelligences, and determine in real time whether new prescriptions are being generated from dispensed samples.

Figure 1:
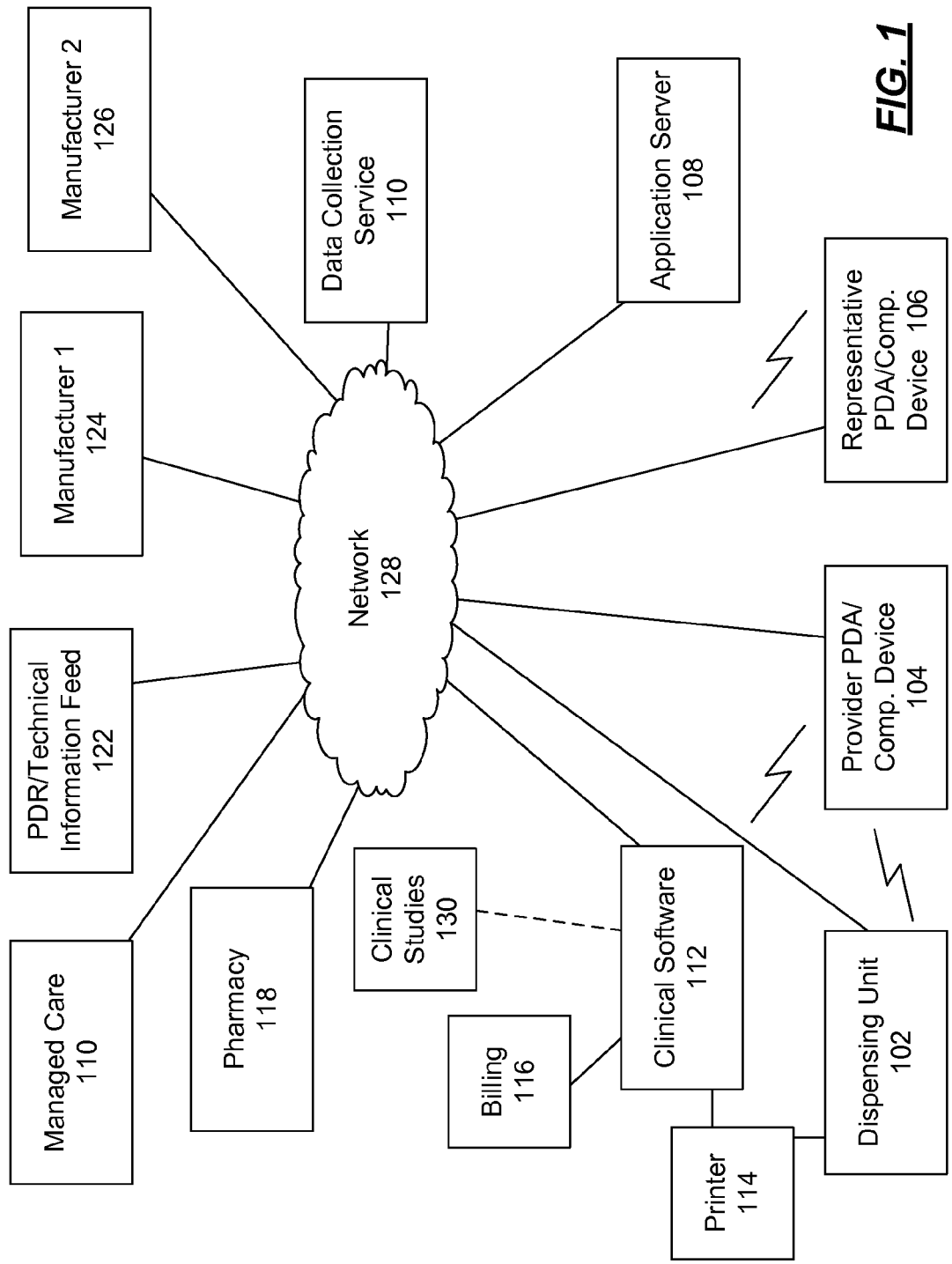
FIG. 1 depicts an example operational environment that may be used to practice aspects of the present disclosure.
Figure 2A:
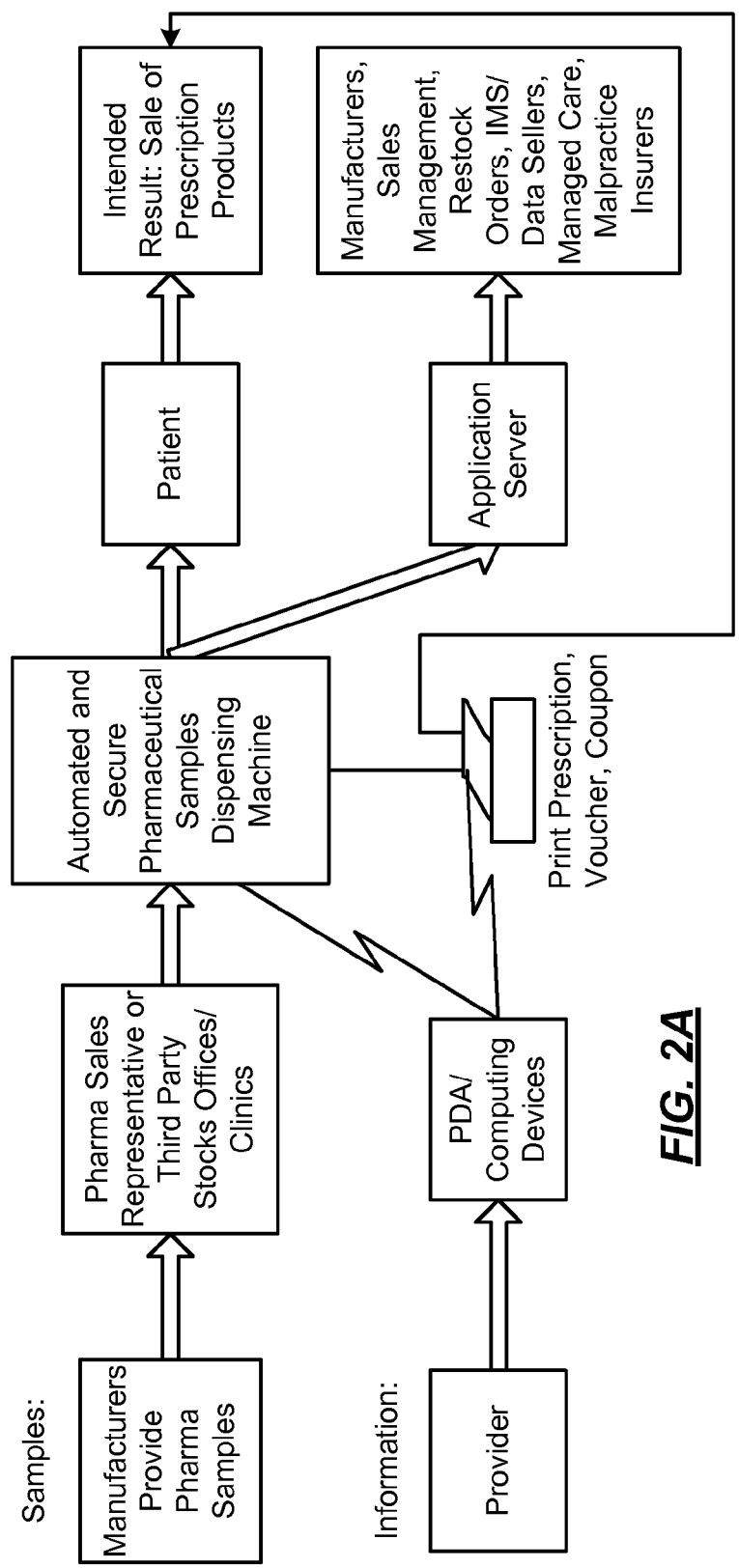
FIGS. 2A-2B illustrate information flows within the example operational environment of FIG. 1.
Figure 2B:
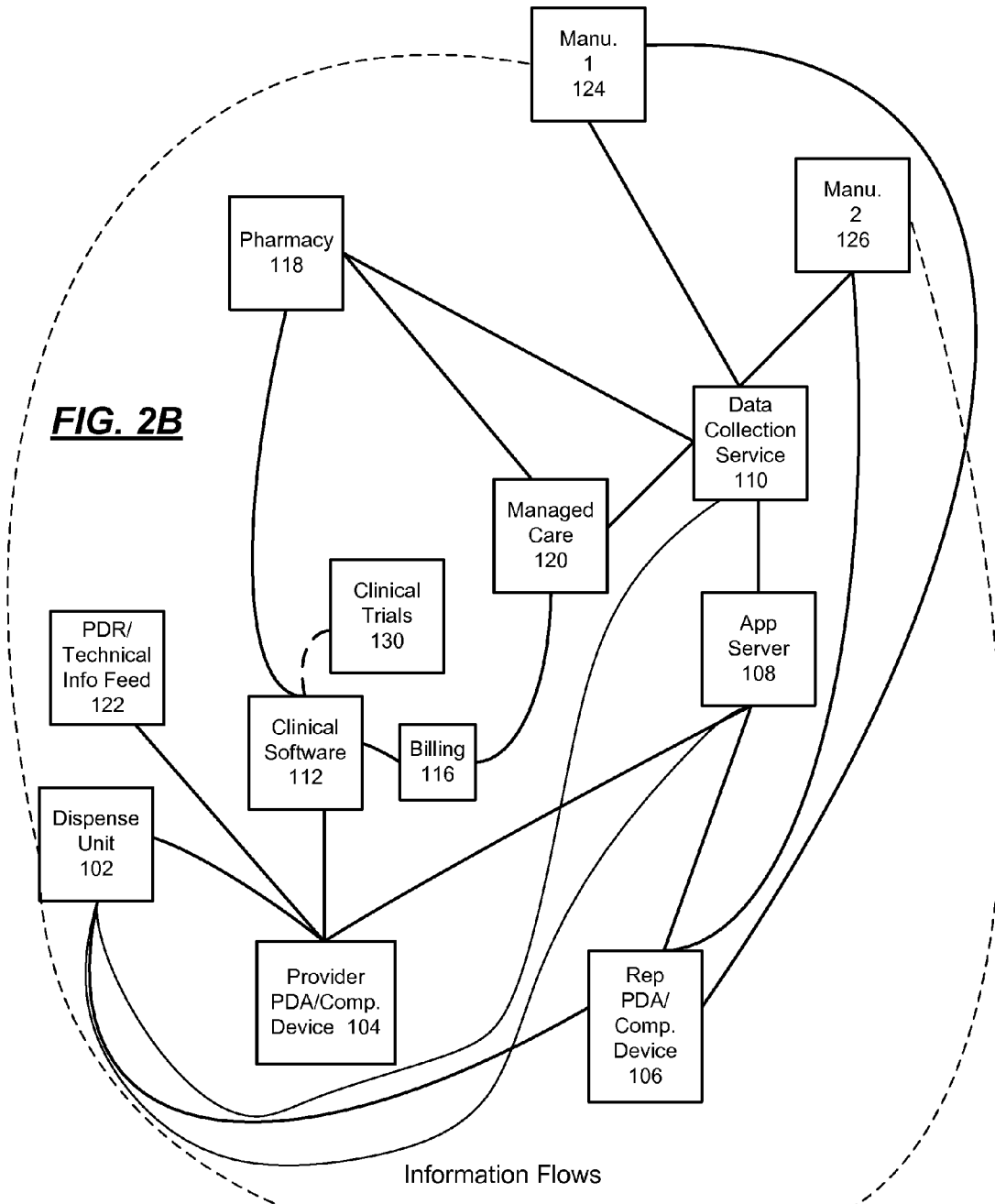

Referring to FIG. 1, there is illustrated an exemplary environment in which aspects of the present disclosure may be implemented. FIGS. 2A and 2B illustrate information flows between the various components, elements and entities in the system.

Representative PDA/Wireless Device/Computing Device (Representative Device) 106

A representative device 106 may be provided that enables field representatives, restocking services or managers to view near real-time sample inventory balances on hand within dispensing units placed in offices. The representative device 106 may receive an automatic alert regarding inventory balance and replenishment requests at pre-set, manufacturer's determined product "break even" points. The representative device 106 may allow field based representatives and managers to view sample trend lines and dispensed sample to new prescription generated ratios using an application server 108 or direct link to a represented manufacturer (e.g., manufacturer 1 or 2, shown by reference numerals 124 and 126, respectively). The representative device 106 may allow a review of product specific information (dosage, indications, and cost), managed care formulary coverage status, and company product alerts.

The representative device 106 may access the above information through a local application running on the device, or through one or more interfaces provided to the representative device 106 by an application server 108. The information may be pushed to the representative device 106 or provided upon request by a user. The representative device 106 may be a wireless handset provided by, e.g., Motorola, Research in Motion, Nokia, HTC, etc. and may run a suitable operating system. In addition, representative device 106 may include a browser application to access the application server 108. The representative device 106 may access mobile networks (e.g., 3G, GPRS, EDGE), wireless networks (e.g., 802.11, 802.16) or wired networks (e.g., Ethernet).

Provider PDA/Wireless Device/Computing Device (Provider Device) 104

The provider device 104 may allow medical providers to view sample balances on hand, product lot numbers, and product expiration dates. Medical providers may dispense patient starters (samples) directly or via a triage nurse or appropriate staff to patients. The provider device 104 may allow the medical provider to filter samples by disease state, FDA approved indications, manufacturer, product name, balances on hand or other criteria for the drugs indicated to specific medical conditions. The provider device 104 may auto populate select samples by managed care formulary coverage status e.g., 1st, 2nd, 3rd tier co-pay, prior authorization (PA), or restricted status (RC).

The provider device 104 may allow medical providers to either electronically transmit a prescription to a pharmacy 118, or to generate a hard copy prescription to be delivered to the patient with samples being dispensing at the point of care.

The provider device 104 may interface with patient assistance programs. Often, if the patient is self-pay, doctors will provide a large quantity of samples to eliminate the need for the patient to fill a prescription. This works against programs set up by pharmaceutical manufacturers to assist those who have difficulties paying for prescription medication. The provider device 104 may populate fields and data within application paperwork to enroll such patients in the special assistance programs. This enhances the likelihood that samples are being used as intended.

The provider device 104 may provide a user interface that is populated with local and regional specialty providers. For example, this option may allow the primary care provider to electronically schedule and confirm patient appointment with specialty physicians. Once an appointment has been set, an auto-populated reminder appointment card may be printed and distributed to the patient. The provider device 104 may provide an electronic option to fill patient assistance requests to both the manufacturer directly or to a designated outside vendor.

Banner ads and other information may be displayed on the provider device 104. Manufacturers (pharmaceutical companies), managed care 120, or other entities may pay priority fees to have the ads or information displayed on the provider (or representative) device. Revenue may be generated from click through fees, promotional fees and/or advertising fees.

The provider device 104 may interface either wirelessly or over a wired connection with clinical software 112 that may be used to store patient records, interface with billing systems 116, provide input to clinical studies 130 (e.g., CDC, JAMA, etc.), provide practice management, generate electronic prescriptions, manage medical imaging systems, etc. Exemplary clinical software is available from Allscripts, LLC, Chicago, Ill.

The provider device 104 may also interface either wirelessly or over a wired connection with a dispensing unit 102 to provide samples to a patient, as described below. The provider device 104 may include the same hardware and networking capabilities as noted with regard to the representative device 106.

Dispensing Unit 102

The dispensing unit 102 may be placed within the medical provider's office and may be programmed to be compatible and interface with pharmaceutical representatives and district manager's wireless devices/PDA in order to facilitate virtually sample audits from remote sites. The dispensing units may be programmed to electronically store, monitor, and dispense professional pharmaceutical patient starters (i.e., samples) using barcodes, RFID, or any other inventory management technique. The dispensing units may include networking capabilities such that they may interface with a conventional network infrastructure (LAN), wireless networks and/or mobile networks 128. The units may be individually addressed and remotely accessed.

The dispensing units may be activated by the physicians PDA/wireless device, or at the dispensing unit by entry of a PIN number, a security token, biometric device, a card swipe, etc., to release select patient samples to a triage nurse or affiliated medical provider.

The dispensing units may transmit an inventory balance alert to the representatives PDA as sample inventories reach a manufacturer's predetermined alerting point. The warning may be provided to a web service (an application server 108) and made available to the representative or the manufacturer.

The dispensing unit 102 may require a manufacturer's issued PIN number, or a card swipe in order to access the units and samples stored within the units. The physical structure of the dispensing unit 102 may include secured compartments or storage bins that may be assigned to participating manufacturers based on initial subscription or renewal of annual contracts. The dispensing units may time stamp replenishment requests, representative to last load or accessed the storage compartment/sample bins, and identifies placed sample inventory by product lot number and bar code. The dispensing unit 102 may sense the content within the unit to ensure that the proper product sample is in a respective bin by weighing the samples, optically reading the samples, etc. to insure accurate dispensing of samples.

The dispensing unit 102 may generate an e-prescription or printed hard copy prescription to be matched to the dispensed samples product lot number or product's bar code. The dispensing unit 102 may match dispensed samples to auto-generated prescriptions. This matching may be performed by tagging the prescription with a barcode, RFID, or any other unique identifier to track the matched sample/prescription pair. This tracking enables pharmaceutical and biotech companies to target select physicians and determine precise return on investment (ROI). This information is also a valuable resource to managed care organizations, and patient assistance programs. In some implementations, patient privacy concerns will prevent the identification of a person to the unique tracking number, as such only the combination of the prescription and sample is tracked.

The dispensing unit 102 may include room temperature and refrigerated compartments. This split structure accommodates oral medications, vaccines and oral suspensions. The dispensing unit 102 may allocate a specific and manufacturer's pre-determined number of sample units per patient, per patient visit. The dispensing unit 102 may automatically provide prescribing information for all samples activated and released by the units. The dispensing unit 102 may have alternative power source in the event of a power outage.

The dispensing unit 102 may also provide drug information to patients. For example, this information may be substantially similar to that provided by pharmacies when a prescription is filled, i.e., information regarding dosage, the drug formulation, side effects, warnings, etc. As such, the likelihood of a patient misusing a sample or having negative effects is reduced.

Stocking or rental fees may be paid by the manufacturers or managed care 120 to place products within the dispensing unit 102. Such fees may be paid to offset the costs of operating the devices or to the data collection service, etc.

The dispensing unit 102 may include a debit card dispenser. Debit cards having a predetermined value may be dispensed based on a sample being dispensed from the dispensing unit 102. The debit cards may be used to purchase pharmaceuticals manufactured by the manufacturer of the sample.

Exemplary dispensing units include, but are not limited to the RoboCrib 1100, available from AutoCrib, Santa Ana, Calif.; and Cubex, available from VSupply, Phoenix, Ariz.

Printer 114

As noted above, the dispensing device may include a printing device to print prescriptions or other information related to the operation or status of the dispensing device. In addition, the clinical software 112 and/or dispensing unit 102 may have access to a stand-alone printing device. Detailed printing device may be used to print prescriptions, coupons paid for by the manufacturers, coupons paid for by local pharmacies, vouchers having prepaid value to purchase pharmaceutical products, "package insert" information, patient satisfaction materials, and/or patient information data capture forms.

Pharmacy/Pharmacy Management System 118

A pharmacy data prescription outflow service may include software compatible with field-based PDA's/computing devices, and that may interface with the back end data system in pharmacies, hospitals, pharmaceutical manufacturers, and managed care organizations. The service may be part of a pharmacy management system, such as that available from McKesson, San Francisco, Calif.

The pharmacy management system 118 may be a hosted (Application Service Provider—ASP) pharmacy management solution for pharmacy users connecting to a centrally hosted system over the Internet using a secure networking technology. Prescription information may be stored in a centralized database. The pharmacy management system 118 may combine pricing, drug updates, a managed care interface for patient insurance information, and inventory allocation. The pharmacy management system 118 may read a bar code, RFID, or other unique identifier (as described above) on the prescription that identifies that the prescription as being associated with a sample dispensed by a dispensing unit 102. The information from the bar code, and other information collected via the dispensing unit 102, may be forwarded to a data collection service that compiles information related to samples provided to doctors that are dispensed to patients, and prescriptions that result from the dispensing of a sample, as described below.

The pharmacy management system 118 may store the unique identifier in a database or transmit it to a data collection service in real-time. If the identifier is stored in the database, it may be transmitted to the data collection service on a periodic basis. The pharmacy management system 118 may communicate the identifier and other relevant information using a standard format, such as XML.

Managed Care 120

Managed care providers may interface with doctor office billing services 116 provided by the clinical software 112, pharmacies and the data collection service. The term "managed care" is used herein to describe providers or companies who finance the delivery of health care to enrollees through contract rates with medical providers, pharmacies and hospitals.

Managed care 120 may provide contract and/or coverage information to the provider device 104 in real time or as part of a periodic data feed. As such, when the provider queries and retrieves information about prescription medication and tier coverages, the patient will be provided accurate information about his/her particular coverage for a prescribed medication. This reduces the likelihood of a patient needing a different prescription and/or sample because a prescribed medication is not covered.

Technical Information Feed 122

A technical information feed 122 may provide information to a health care provider as a downloadable component to the health care provider PDA/computing device. For example, the Physician's Desk Reference may be downloaded to the PDA/computing device through a service such as Thomson Clinical Xpert, available from Thomson Healthcare, Montvale, N.J., or the Sanford Guide to Antimicrobial Therapy, available from Anitmicrobial Therapy, Inc. Sperryville, Va. The PDR may be used an evidence-based application for the PDA/computing device that includes clinical references and point-of-care tools. The information may enable a provider to query and display drug information, drug interactions, toxicology information, a disease database and alternative medicines.

Manufacturers

Manufacturer 1 and manufacturer 2 (reference numerals 124 and 126, respectively) may be pharmaceutical companies that research, manufacture and/or sell pharmaceutical products. The manufacturers may provide samples of the products to medical providers, who in turn, may provide the samples to patients.

The manufacturers may have backend systems, such as SAP Business Suite, available from SAP Americas, Newtown Square, Pa. The backend systems may monitor, plan, schedule, sequence, and execute a variety of manufacturing processes involved with the production of pharmaceutical products. The backend system may also provide a customer relationship module and a supply-chain management module that manages customers, such as physicians, hospitals and other medical providers, as well as the samples that are provided to the customers. The backend system may receive information from the representative device 106, either directly or through an application server 108 regarding samples provided to medical providers.

The backend systems may interface with the billing system 116 to automatically invoice accounts when the dispensing unit 102 is restocked. For example, when a representative restocks the dispensing machine with, e.g., vaccines, the provider PDA/computing device 104 may communicate to the backend system with an amount and product restocked into the dispensing unit 102. The backend system may invoice the billing system 116 such that the manufacturer can be paid for the product.

Data Collection Service

A data collection service serves as an information depot for prescription data flowing out of matched sample to generated prescriptions. The prescriptions may be filled at pharmacies, mail order fulfillment sites, and specialty locations. This information may be provided to other third parties (e.g., IMS). Aggregated data involving dispensed samples, filled prescriptions, and medical outcomes may be provided to regulatory and governmental health agencies. Outflow prescription data captured may be provided to managed care organizations.

Information linked to samples being dispensed through the system may be uploaded to the pharmaceutical and biotech companies compliance departments (e.g., at manufacturer 1 or 2), field representative and managers remote devices, and the distribution warehouses. This feature of system provides for accountability of distributed samples, minimizes the potential for sample outage, and provides a time management tool for field-based personnel.

The data collection service may also gather information about patient demographics, the medical providers who dispense samples that result in filled prescriptions for pharmaceuticals, the representatives who provide the samples to medical providers, the percentage of samples that are actually dispensed to patients relative to the number of samples provided by the manufacturers to the representatives, the pharmacies who receive prescriptions based on dispensed samples, etc. One of ordinary skill in the art would understand that there are many data points of interest to a manufacturer who provides samples. The data collection service may gather any or all such data points and make them available. Such data points may be used to optimize the flow of samples from the manufacturer through the representatives to medical providers in order to maximize the manufacturer's return on investment.

Application Server 108

The application server 108 is a software engine that delivers applications to client computers or devices, typically through the Internet and using the HyperText Transfer Protocol. The application server 108 handles most, if not all, of the business logic and data access of an application.

Application servers typically bundle middleware to enable applications to intercommunicate with dependent applications, like web servers, database management systems, and chart programs. The application server 108 may also provide an application programming interface (API) to make it operating system independent. The application server 108 may run a Java Platform—Enterprise Edition (J2EE) or Java EE 5 application server, such as JBoss (Red Hat), WebSphere Application Server (IBM), Sun Java System Application Server (Sun Microsystems), the SAP Web Application Server, or .NET Framework (Microsoft).

A Java Server Page (JSP) is a servlet from Java that executes in a Web container—the Java equivalent of CGI scripts. JSPs are a way to create HTML pages by embedding references to the server logic within the page. JavaBeans are independent class components of the Java architecture from Sun Microsystems.

Although FIGS. 2A and 2B only illustrate a connection with the data collection service, the application server 108 may provide an interface to any of the systems illustrated in FIGS. 1, 2A and 2B. For example, the application server 108 may provide an interface to manufacturer's backend systems such as to allow a representative, using the representative device 106 to upload information about samples delivered to medical providers to the manufacturer. Also, the representative may access the application server 108 to determine the status of dispensing units throughout a representatives' area of coverage to determine if any of the units need to be restocked or are suffering any problems.

The data collection service may use the application server 108 to provide information to manufacturers, representatives, medical providers or other parties. As noted above, manufacturers are interested in information such as the number of samples dispensed that result in actual prescriptions being filled by patients. The manufactures may access the information through a user interface provided by the application server 108, or directly receive the information from the application server 108 using the manufacture's backend system for further processing and/or analysis. The manufacturer may also access the application server 108 to ascertain information about the medical providers who are dispensing the manufacturer samples.

The application server 108 may also be used as part of a physician participation plan, where physicians who utilize the sample dispensing system may be eligible for a negotiated premium discount with medical malpractice insurance carriers.

The system described with reference to FIGS. 1, 2A and 2B is merely one example of a system to collect data and dispense controlled substances, and other various are within the scope of the present disclosure.

Figure 3:
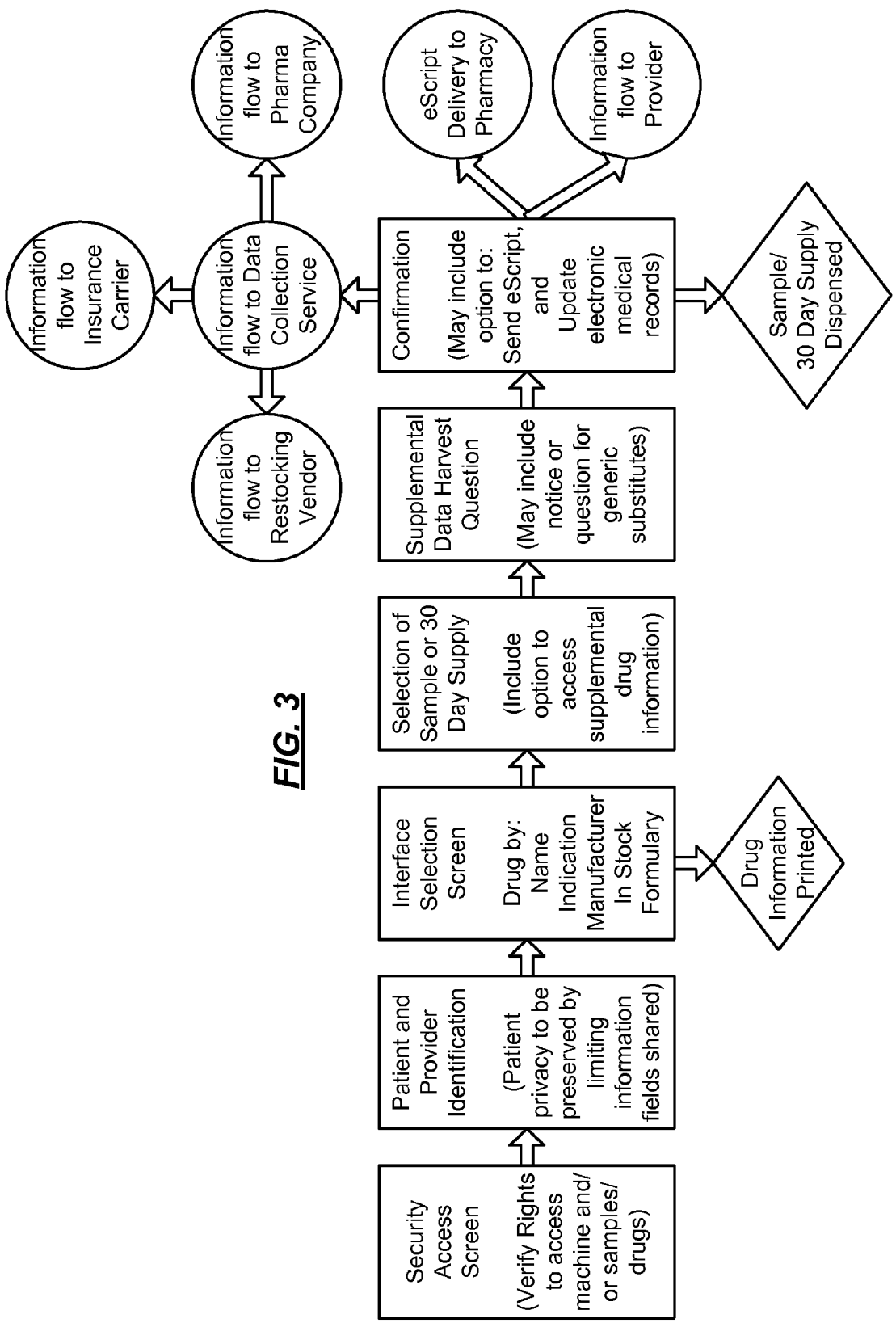
FIGS. 3-10 depict operational flowcharts illustrating implementations of the present disclosure.

FIG. 3 illustrates a high-level overview of the general process flow whereby a medical provider may enter information into the provider device 104 to dispense a sample or other quantity of medical supplies from the dispensing unit 102. In addition, as shown in FIG. 3, after the supply is dispensed, information regarding the dispensing (e.g., a sample that was dispensed), prescription information and other information flows then take place as described above with regard to FIGS. 1, 2A and 2B. It is noted that FIG. 3 illustrates an example process and other processes would be evident to those of ordinary skill in the art in view of the present disclosure.

As shown in FIG. 3, initially a security access screen may be presented on the provider device 104. A security access screen may be presented to verify rights and access to the dispensing machine and system services. Next, patient and/or provider information may be requested and/or provided. This information may identify the patient and/or provider, and may be requested in compliance with privacy regulations. After the patient and or provider information has been provided, an interface selection screen may be presented. The interface selection screen may identify drugs or medications available in the dispensing unit by name, indication, manufacturer, availability, and/or formulary.

After presenting the interface selection screen, a physician and/or medical provider may make a selection of a sample or other supply of controlled substances. Drug information may be printed by the dispensing unit printer 114 and/or an attached printing device. Supplemental drug information may also be provided at this stage. For example, generic substitutes may be provided for brand-name medicines. The medical provider may thus be able to select a suitable generic for dispensing. Next, a confirmation is presented on the provider device 104. The confirmation may include an option to send electronic e-prescription to a pharmacy, and/or an option to update electronic medical records associated with the patient.

One or more actions and or information flows may then occur upon presenting the confirmation screen. For example, the sample (or supply of medicine) may then be dispensed from the dispensing unit 102. Information may be sent to manage care regarding the medicine dispensed. The electronic prescription may be delivered to a selected pharmacy.

In addition, the data collection service may receive information regarding all or some of the events that occurred during the encounter with the patient. For example the data collection service may collect information regarding the medicine dispensed, whether a prescription was generated, the illness for which the dispensed medicine is intended to treat, health and status information regarding dispensing unit, etc.

As described in FIGS. 2A and 2B, there are many information flows that occur within the system. It is intended that any or all of the information flowing through the system may be captured and correlated by the data collection service for use by any of the entities described above. For example, as shown in FIG. 3, information flows to data collection service may be provided to a dispensing entity in a restocking vendor (a pharmaceutical representative, or other), managed care (HMO or other insurance company) and/or the manufacturers (pharmaceutical companies).

FIGS. 4-10 illustrate exemplary operation flow diagrams that describe operations performed by various components illustrated in FIGS. 1, 2A and 2B. In addition, FIGS. 4-10 build on aspects of FIG. 3 and describe such aspects in greater detail or in alternatives. It is noted that FIGS. 4-10 illustrate example processes and other processes would be evident to those of ordinary skill in the art upon in view of the present disclosure.

Figure 4:
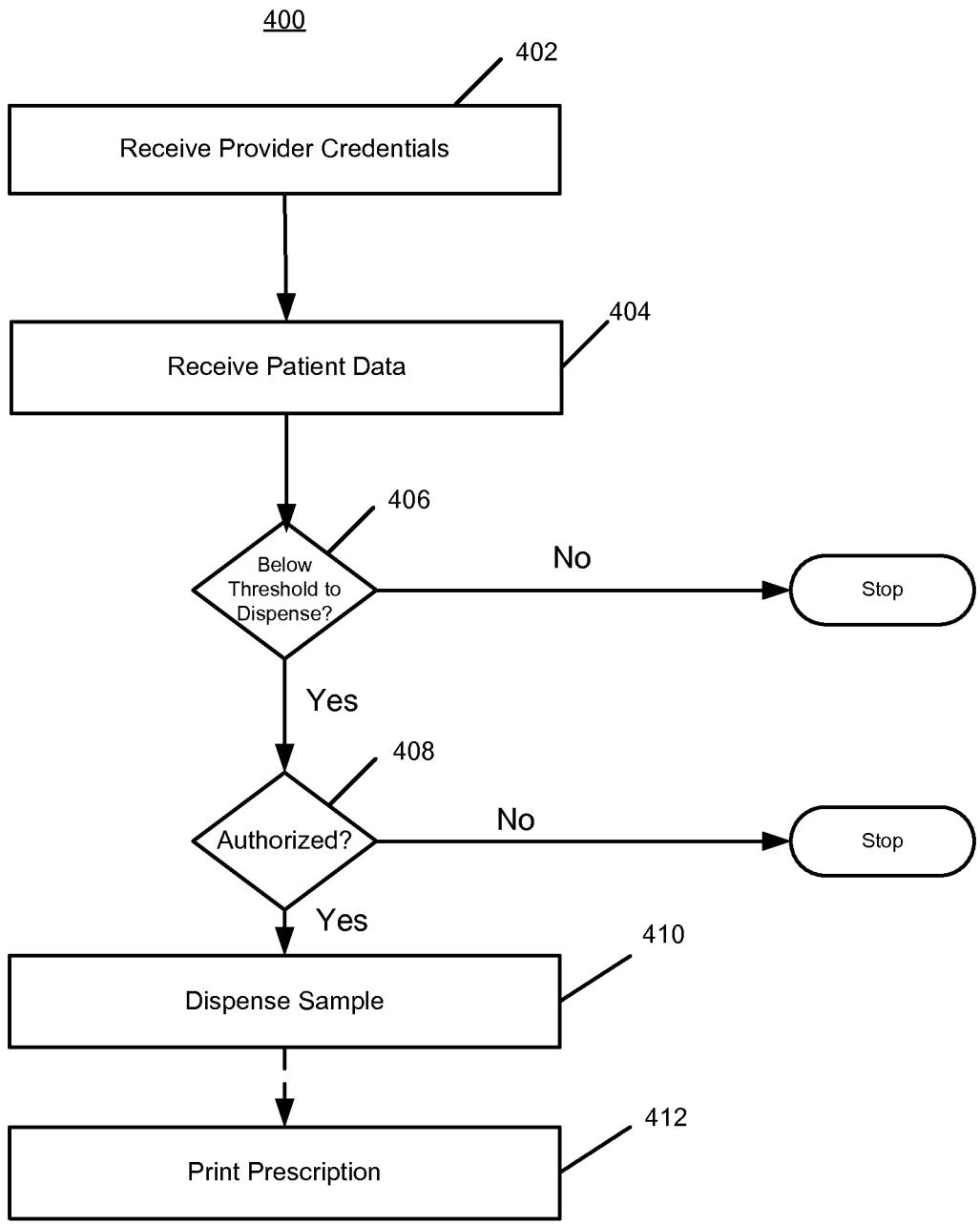

Referring now to FIG. 4, there is illustrated an exemplary process flow 400 associated with a dispensing unit and an authorization to dispense. The process begins at 402, where provider credentials are received. The credentials may be received as an ID and password combination, biometric information, barcode, etc. The provider credentials may be credentials associated with the doctor, physician's assistant, or other medical provider. At 404, patient data is received. The patient data may be information such as name, date of birth, address, insurance provider, etc. At 406, it is determined if enough information regarding the patient has been received. If not enough information has been provided the process may stop. However, if at 406 enough information has been provided regarding the patient, then at 408, a check of the credentials may be made. If the provider is not authorized the process may stop. However, if the provider is authorized, then at 410, a sample may be dispensed from the dispensing unit. Optionally or additionally, a prescription may be printed by the dispensing unit or a stand-alone printer 114. Optionally or additionally, a prescription may be electronically communicated to a pharmacy of choice.

Figure 5:
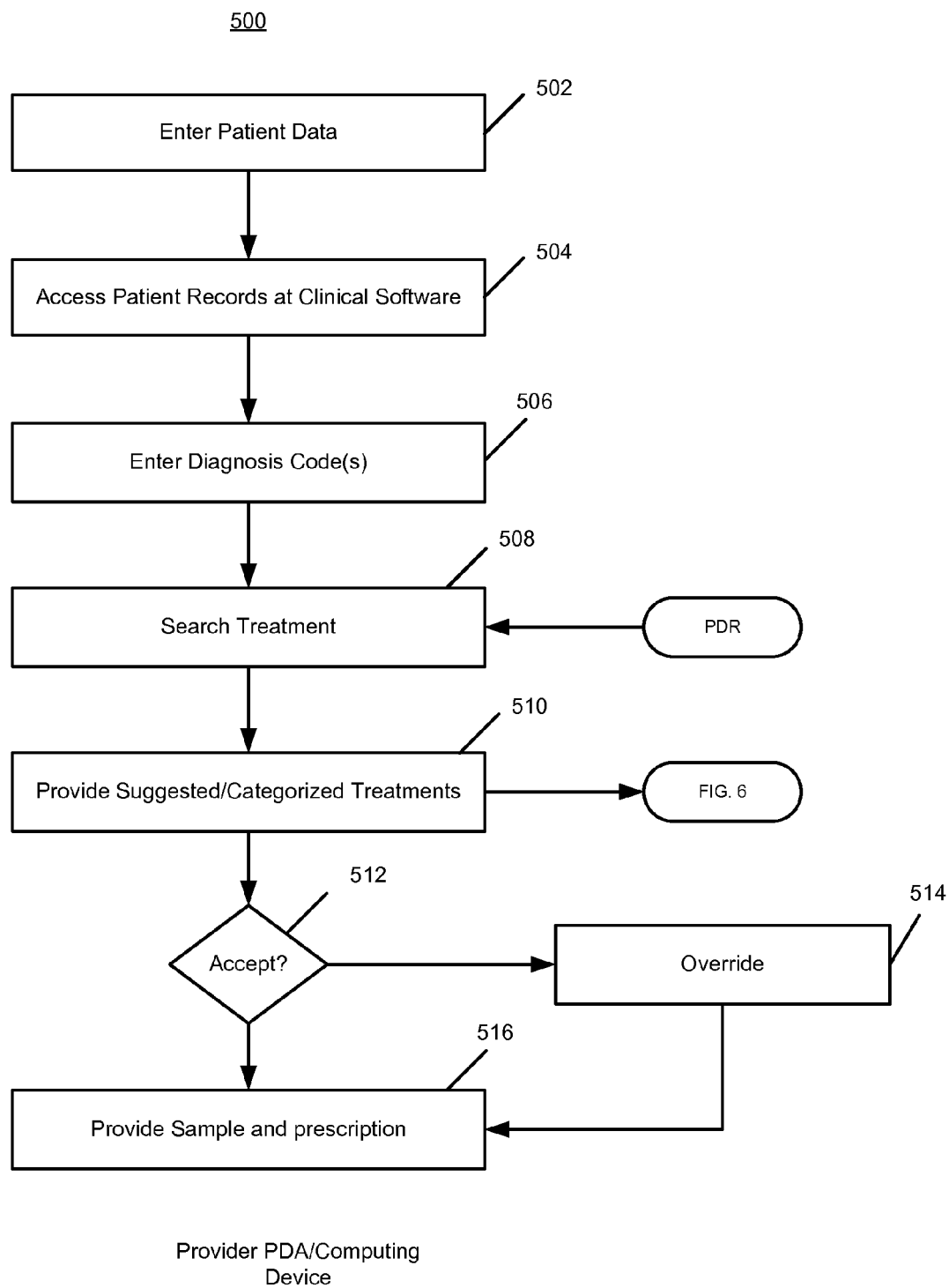
Figure 6:
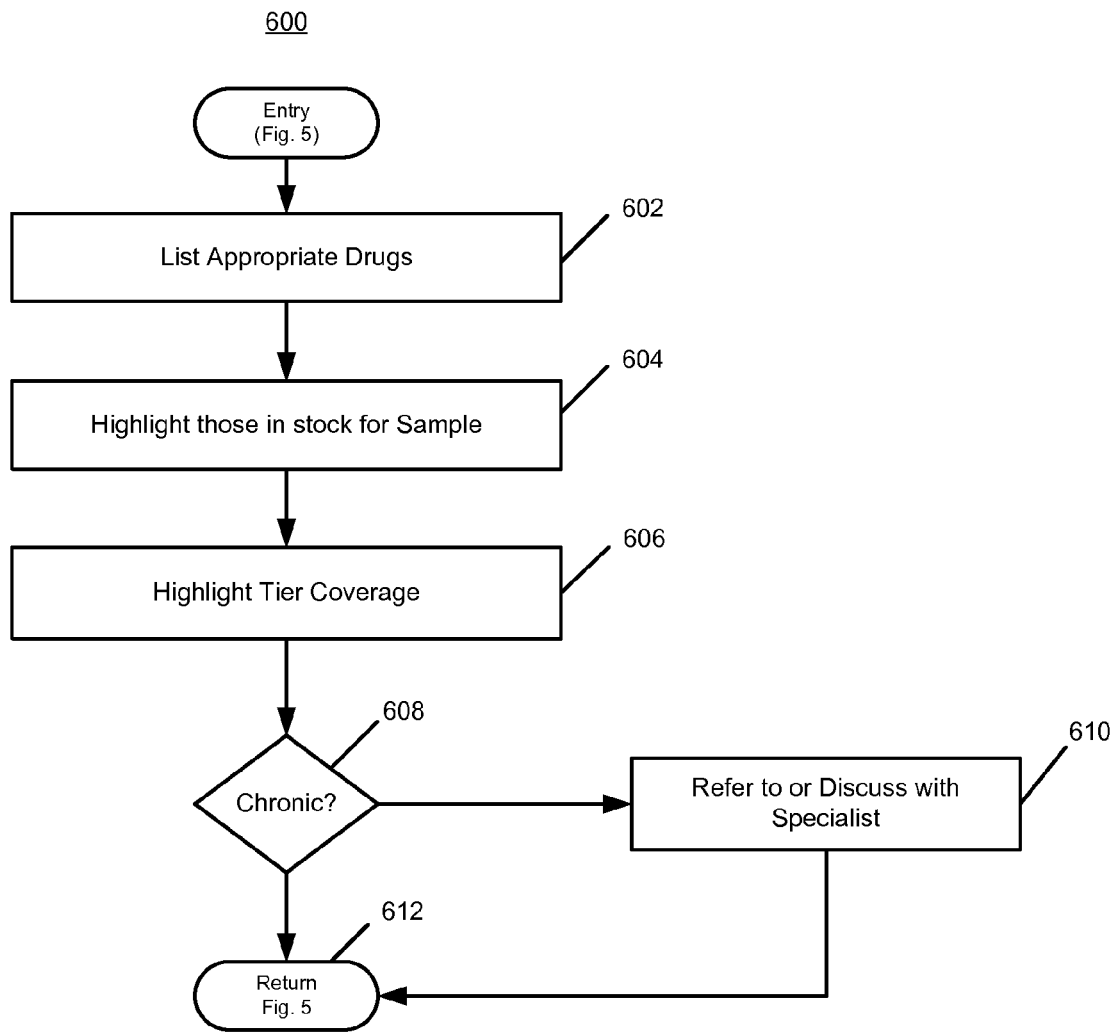

Referring to FIGS. 5 and 6, there is illustrated process flows 500 and 600 associated with the provider device. At 502, patient data is entered into the provider device. At 504, using the patient data, patient records are accessed by clinical software 112 at the medical provider's location. At 506, a medical provider may enter diagnosis codes associated with the patient under examination. At 508, a treatment may be searched. For example, be provider device may take information from the Physicians' Desk Reference (PDR) and search for information for a treatment associated with the enter diagnosis codes.

At 510, suggested treatments may be presented on the provider device. For example, these suggestions may be provided in accordance with the process flow 600 shown in FIG. 6. At 602, a list of appropriate drugs may be presented on the provider device. For the convenience of the medical provider, at 604, those in stock (i.e., if available within the dispensing unit) may be highlighted. Optionally or additionally, at 606 tier coverages associated with the appropriate drugs may be provided. The tier coverages may be made available to the provider device from managed care in order to guide the medical provider into an appropriate drug and/or to provide the patient with information regarding co-pays, etc., associated with the drug to be administered. At 608, it may be determined if the patient is chronic. For example, if the patient has returned to the medical provider for the same symptoms more than a threshold number of times, then at 610, a recommendation to refer to, or discuss with, a specialist may be made. If the patient is not chronic at 608, then the process returns to 510 where the medical provider may accept the recommendations at 512. If a medical provider accepts the recommendations, a sample of the recommend drug may be dispensed from the dispensing unit and a printed at 516. If a medical provider does not accept the recommendation, then at 514 the recommend drug may be overridden with a different preference, and then dispensed at 516 together with a prescription.

Figure 7:
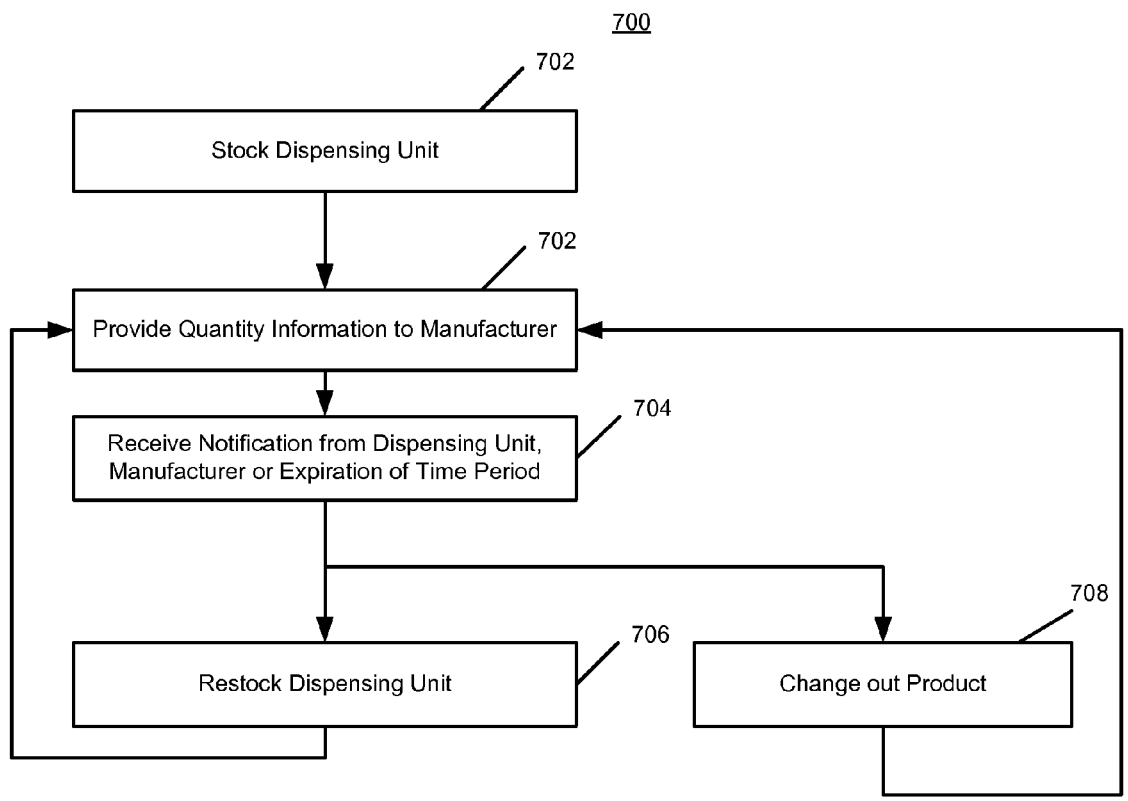

Referring now to FIG. 7, there is illustrated an example process 700 associated with the representative device 106. The representative device 106 may be used by a pharmaceutical representative and/or a restocking vendor in combination with the dispensing unit. At 702, the dispensing unit is stocked. At 704, through one of the information flows, quantity information regarding the stocking of the dispensing unit may be provided to the appropriate manufacturer. At 706, a notification may be received from the dispensing unit, manufacture, or upon the expiration of a time period that the dispensing needs to be restocked (708) or that product needs to be changed-out (710).

For example, the dispensing unit may send a notification based on information obtained by reading a barcode, RFID, or other identifier associate with a product contained within the dispensing unit that provides to the dispensing unit expiration information regarding the product. Manufacturers may use lot numbers or other identifiers to indicate when products expire. Thus, knowing which lot numbers were stocked into the dispensing unit, the manufacturer may notify a representative or restocking vendor to change-out product contained within the dispensing unit.

As one of ordinary skill in the art would understand, many different types of notices may be sent to the representative device 106 regarding quantity levels of product contained within dispensing units and/or other information regarding the product to notify the representative or restocking vendor that a particular dispensing device requires restocking or change-out of expired product.

Figure 8:
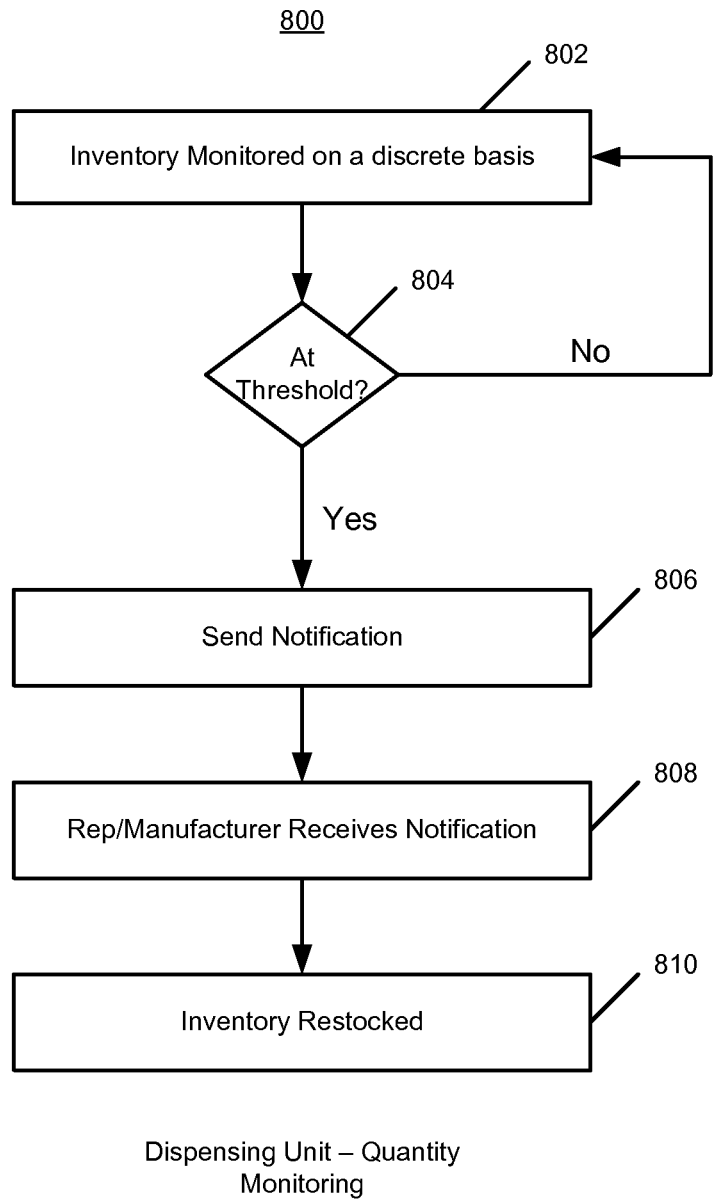

FIG. 8 illustrates an example process 800 that may be executed within the dispensing unit for monitoring inventory within in the dispensing unit. At 802, inventory may be monitored on a discrete basis. For example, each individually packaged product within the dispensing unit may be monitored for one or more factors, e.g., expiration date, etc. At 804, it is determined if any one of the factors is at a threshold. The threshold may be a total number of samples within the dispensing unit, an expiration date of one or more of the products within dispensing unit, a maximum time for which a sample or product may be within the dispensing unit, etc.

At 806, if a threshold is met by one or more of the products within the dispensing unit, a notification may be sent to a representative, a restocking vendor, or a medical provider. At 808, the representative, the restocking vendor or the medical provider receives the notification at a respective device. At 810, the representative, the restocking vendor or the medical provider physically restocks the dispensing device. The act of restocking the dispensing device may create an information flow that notifies the data collection service, manufacturer, managed care, etc., of the restocking event and what product(s) was restocked.

Figure 9:
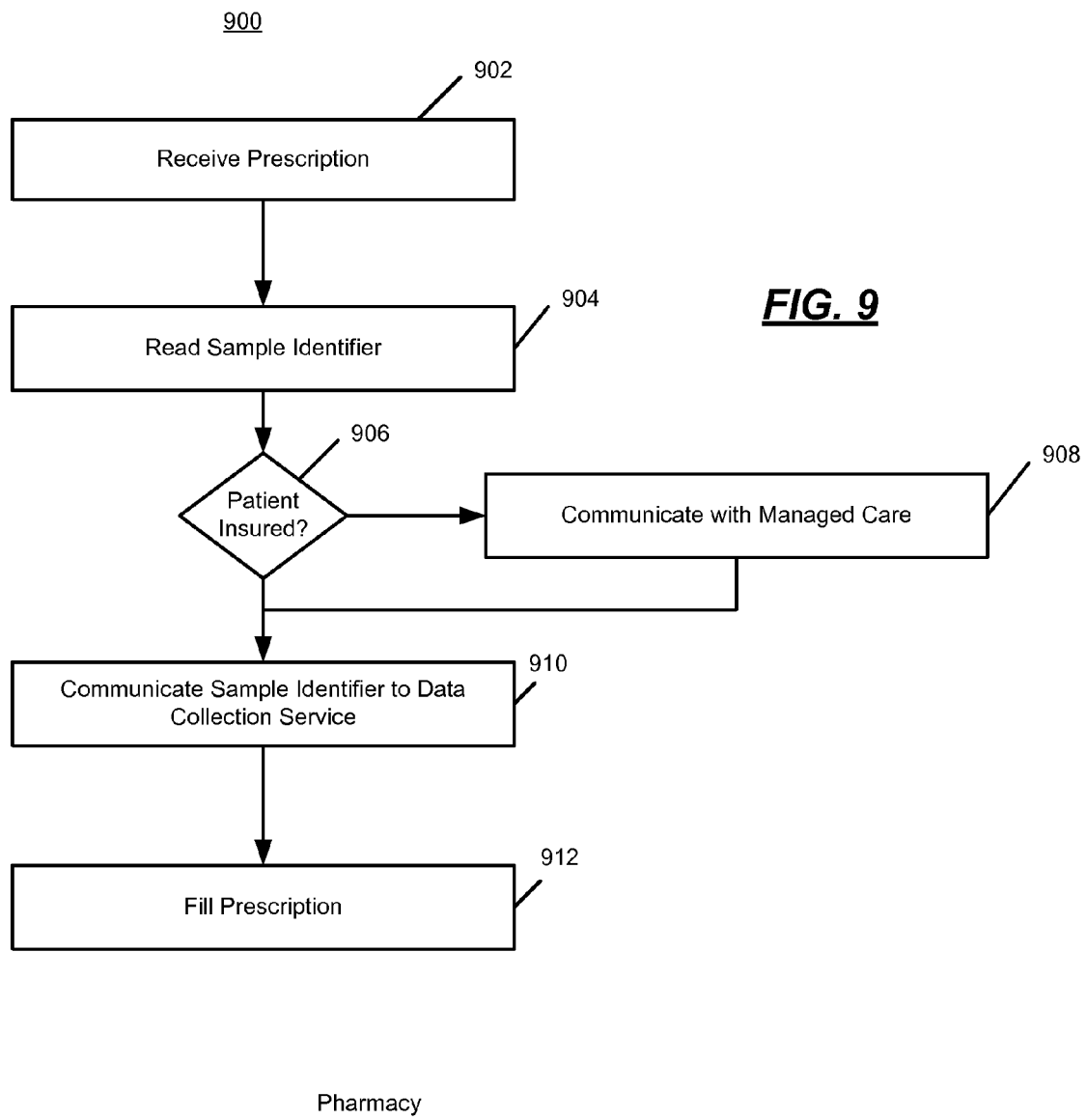

FIG. 9 illustrates an example process flow 900 for receiving a prescription at a pharmacy. At 902, the prescription is received at a pharmacy. The prescription may be a paper copy generated by a printer 114 associated with the dispensing unit or an electronic copy communicated from the dispensing unit and/or medical provider to the pharmacy as part of the processes described above. At 904, a sample identifier is read. The sample identifier may be some unique identifier (e.g., a barcode, an alphanumeric indicator, or other) of the sample that is embedded into the prescription that identifies the sample as coming from the dispensing unit. The identifier may be an electronic indicator if the prescription is an e-prescription.

At 906, it is determined if the patient is insured. The process at 906 may be performed as known in the art to determine applicable insurance coverages of individuals having prescriptions filled (e.g., communicating with managed care at 908). At 910, the sample identifier may be communicated to the data collection service. As one of the information flows, the sample identifier, which identifies a sample as coming from a dispensing unit, may be communicated to the data collection service. The simple identifier may also identify the product (medicine, name brand, generic, etc.) dispensed and other information that may be of interest to manufacturers, managed care, clinical studies, etc. At 912, the pharmacy fills the prescription. The process at 912 may be performed using procedures known in the art.

Figure 10:
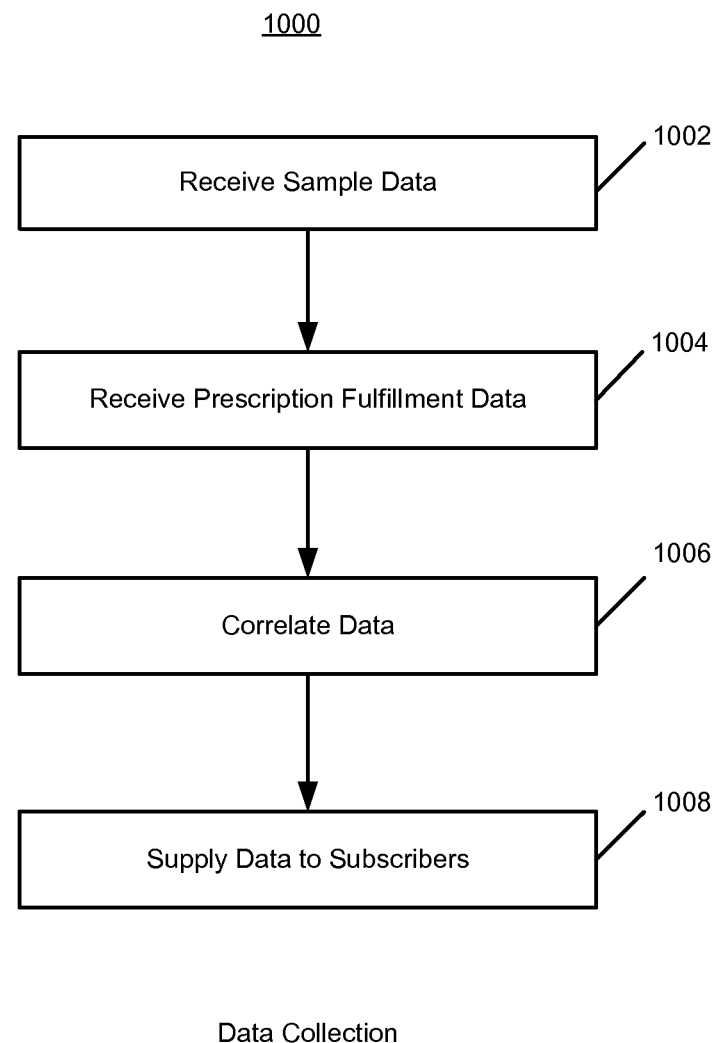

FIG. 10 illustrates a process 1000 for receiving, correlating, and providing data accumulator from the dispensing unit, the provider device, the representative device 106, clinical software 112, and other sources. At 1002, the data collection service may receive sample data (collectively meaning any or all data associated with the dispensing of a sample, as noted above). At 1004, prescription fulfillment data may be received. This information may be provided by a pharmacy, as noted above. At 1006, the data collection service may correlate data received at 1002 and 1004. The correlation of data may be any statistical analysis or compilation of data packets the information in the form most suitable for end consumer or subscriber. Alternatively or additionally, the correlation of sample to prescriptions may be accomplished at the dispensing unit.

For example, manufactures may be interested in information regarding numbers of their products being dispensed by the dispensing unit, prescribed by medical providers, and where there is fulfillment of the prescription by a pharmacy. Manufactures may also be interested in information regarding actual sample quantities being dispensed by medical providers in relation to the samples manufactured. Managed care may be interested in a number of generics being dispensed as substitutes for name-brand pharmaceutical products. Managed care may also be interested in information regarding which medications (name brand or generic) are being prescribed for which illnesses as an effort for tailoring tier coverage, for example. Yet further, technical information sources may be interested in learning how medications are being used in the field to update and create more accurate diagnostic aids.

Thus, as described above, there is provided a system and methods for dispensing controlled substances (samples and supplies of medication, vaccines, etc.), and capturing, distributing and providing data associated with the controlled substances to and subscribers.

Exemplary Networks/Application Servers

Figure 11:
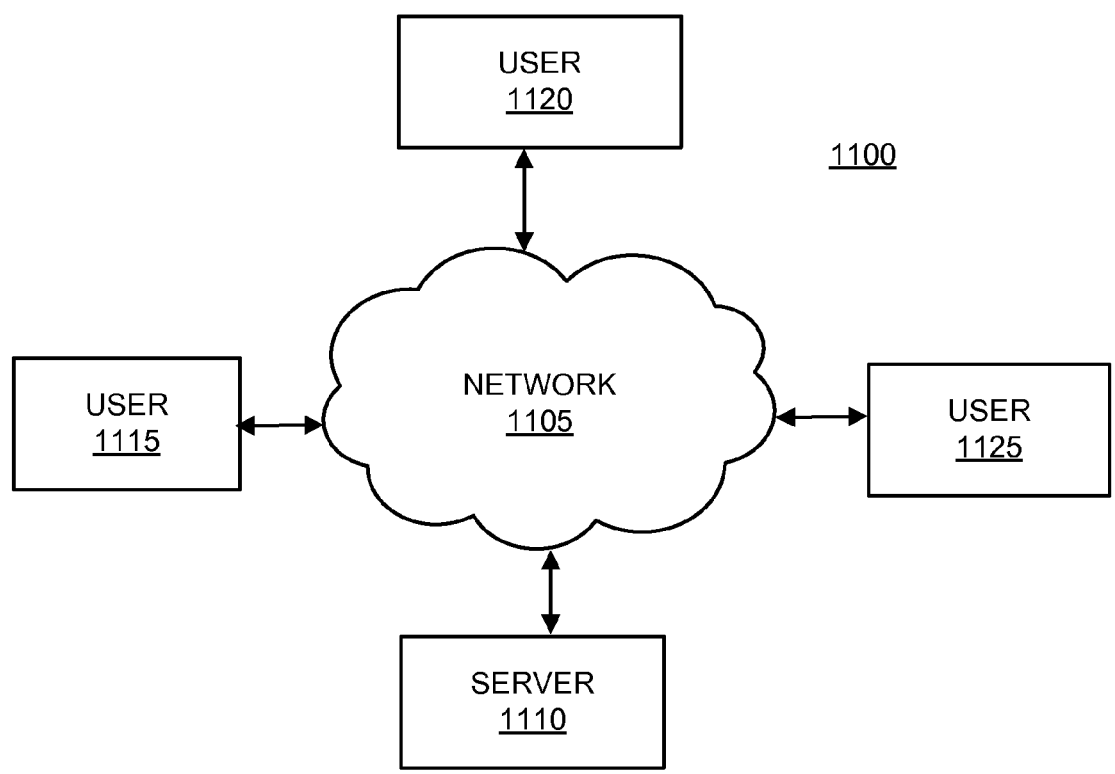
FIG. 11 is an overview of an exemplary network environment that may be used as the network of FIG. 1.

Referring now to FIG. 11, there is an overview of an exemplary network environment that may be used as the network of FIG. 1. The environment includes a computer network 1105 such as, for example, a Transport Control Protocol/Internet Protocol (TCP/IP) network (e.g., the Internet or an intranet.) A server 1110 (e.g., application server, backend server, database server, clinical software server) may be operably coupled to the network 1105 and a plurality of users 1115, 1120, and 1125 (provider device 104, representative device 106) may also be operably coupled to the network 1105 in order to allow communication between the users 1115, 1120, and 1125 and the server 1110.

Each of the server 1110, and the users 1115, 1120, and 1125 include a respective network interface for communicating with the network 1105 (e.g., outputting information to, and receiving information from, the network 1105), such as by transferring information (e.g., instructions, data, signals) between such users 1115, 1120, and 1125 and the network 1105. Accordingly, through the network 1105, the server 1110 communicates with the users 1115, 1120, and 1125, and the users 1115, 1120, and 1125 communicate with the server 1110.

For clarity, FIG. 11 depicts only one server 1110. However, the system may include a plurality of servers that are substantially identical to the server 1110. Likewise, for clarity, FIG. 11 depicts only three users 1115, 1120, and 1125. However, the system may include a plurality of users that are substantially identical to the users 1115, 1120, and 1125.

Each of the server 1110 and the users 1115, 1120, and 1125 may be implemented in various electronic circuitry components and/or software components. For example, the users 1115, 1120 and 1125 may be operating a server computer, a personal computer (e.g., a desktop computer or a portable computer such as, for example, a laptop computer), or a handheld computer.

Figure 12:
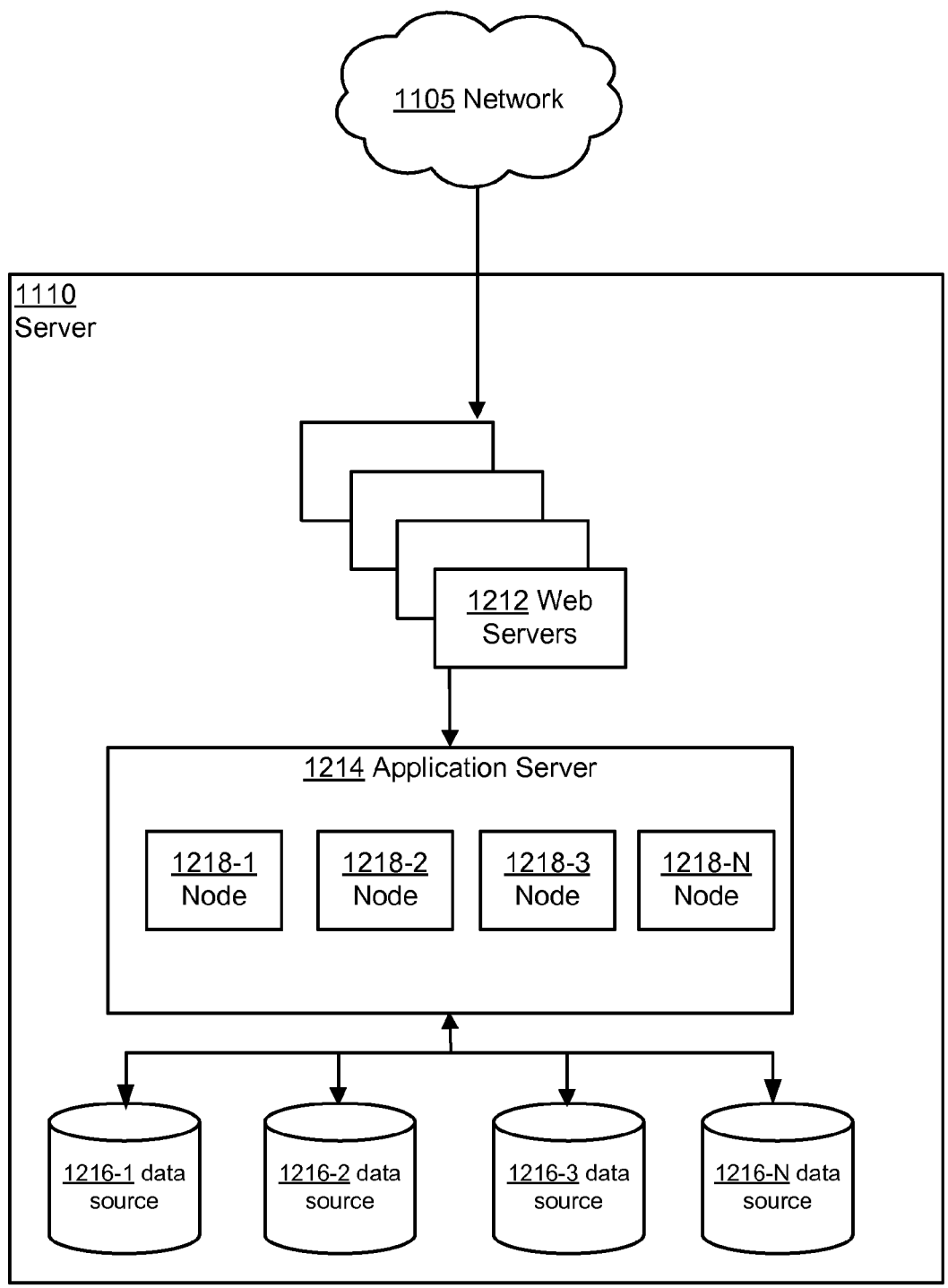
FIG. 12 illustrates the server of FIG. 11 in more detail.

Referring now to FIG. 12, the server 1110 is illustrated in more detail. For example, one or more web servers 1212 such as, for example, Hyper Text Transfer Protocol (HTTP) servers, may be maintained by the server 1110, and may be operably coupled to the network 1105, described above with reference to FIG. 11. In some implementations, an application server 1214, e.g., a WebSphere Application Server available from IBM Corp., may be maintained by the server 1110, and may be operably coupled to the web server(s) 1212.

In some example implementations, the application server 1214 can include one or more nodes 1218-1 through 1218-N (where N is an integer greater than 1), e.g., logical machines, and/or physical machines that can include one or more virtual machines configured to service requests received from clients such as logon requests, request to view account info, etc. For example, the requests may be received from one of users 1115, 1120 and 1125.

When a request is received by a node, node 1218-1 for example, the node 1218-1 carries out the requested function by accessing one or more data sources 1216-1 through 1216-N (where N is an integer greater than 1) to perform an action, e.g., a read/write request, etc. In some implementations, each node 1218-1 through 1218-N can include a java database connectivity API (JDBC), or a java connector architecture (J2C) configured to query data sources 1216-1 through 1216-N. In some implementations data sources 1216-1 through 1216-N may be located remote from the server 1110, and may be operably coupled to the server 1110. Thus, as the web server(s) 1212 receive requests, they can route the requests to a specific node that is configured to handle such request, and the node can access the appropriate data source to perform the desired function.

Exemplary Computing Arrangement

Figure 13:
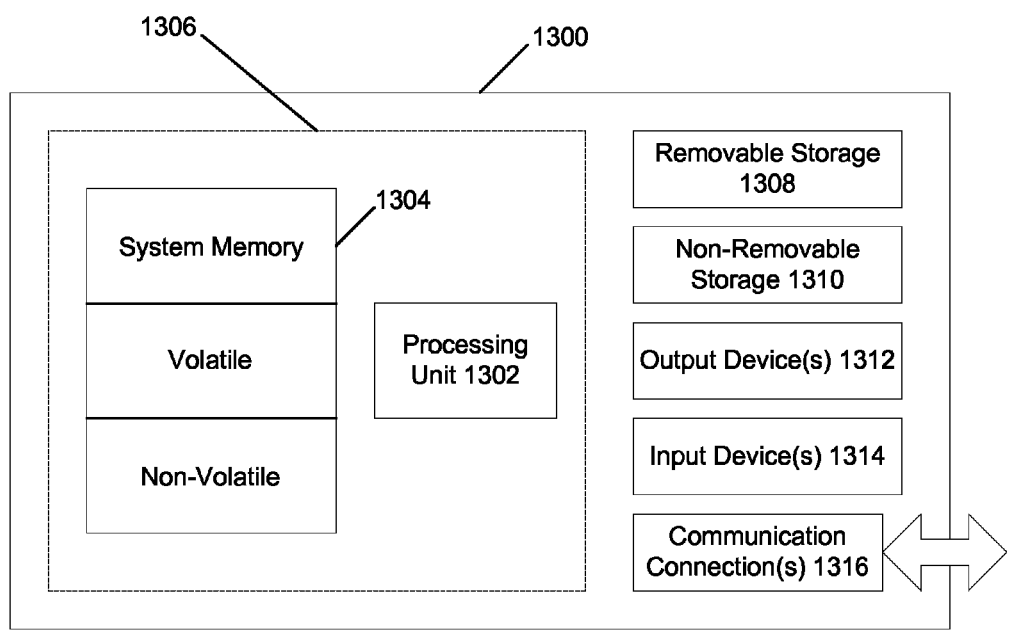
FIG. 13 is a block diagram of an example computing environment in which example aspects may be implemented.

FIG. 13 shows an exemplary computing environment in which example implementations and aspects may be implemented. The computing system environment is only one example of a suitable computing environment and is not intended to suggest any limitation as to the scope of use or functionality.

Numerous other general purpose or special purpose computing system environments or configurations may be used. Examples of well known computing systems, environments, and/or configurations that may be suitable for use include, but are not limited to, PCs, server computers, handheld or laptop devices, multiprocessor systems, microprocessor-based systems, network PCs, minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 13, an exemplary system for implementing aspects described herein includes a computing device, such as computing device 1300. In its most basic configuration, computing device 1300 typically includes at least one processing unit 1302 and system memory 1304. Depending on the exact configuration and type of computing device, system memory 1304 may be volatile (such as random access memory (RAM)), non-volatile (such as read-only memory (ROM), flash memory, etc.), or some combination of the two. This most basic configuration is illustrated in FIG. 13 by dashed line 1306.

Computing device 1300 may have additional features and/or functionality. For example, computing device 1300 may include additional storage (removable and/or non-removable) including, but not limited to, magnetic or optical disks or tape. Such additional storage is illustrated in FIG. 13 by removable storage 1308 and non-removable storage 1310.

Computing device 1300 typically includes a variety of computer-readable media. Computer-readable media may be any available media that may be accessed by computing device 1300 and includes both volatile and non-volatile media, and removable and non-removable media. By way of example, and not limitation, computer-readable media may comprise computer storage media and communication media.

Computer storage media include volatile and non-volatile, and removable and non-removable media implemented in any method or technology for storage of information such as computer-readable instructions, data structures, program modules or other data. System memory 1304, removable storage 1308, and non-removable storage 1310 are all examples of computer storage media. Computer storage media include, but are not limited to, RAM, ROM, Electrically Erasable Programmable Read-Only Memory (EEPROM), flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1300. Any such computer storage media may be part of computing device 1300.

Computing device 1300 may also contain communication connection(s) 1312 that allow the computing device 1300 to communicate with other devices. Communication connection(s) 1312 is an example of communication media. Communication media typically embody computer-readable instructions, data structures, program modules, or other data in a modulated data signal such as a carrier wave or other transport mechanism, and include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, radio frequency (RF), infrared, and other wireless media. The term computer-readable media as used herein includes both storage media and communication media.

Computing device 1300 may also have input device(s) 1314 such as a keyboard, mouse, pen, voice input device, touch input device, etc. Output device(s) 1316 such as a display, speakers, printer, etc. may also be included. All these devices are well known in the art and need not be discussed at length here.

Computing device 1300 may be one of a plurality of computing devices 1300 inter-connected by a network. As may be appreciated, the network may be any appropriate network, each computing device 1300 may be connected thereto by way of communication connection(s) 1312 in any appropriate manner, and each computing device 1300 may communicate with one or more of the other computing devices 1300 in the network in any appropriate manner. For example, the network may be a wired or wireless network within an organization or home or the like, and may include a direct or indirect coupling to an external network such as the Internet or the like.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., using an application programming interface (API), reusable controls, or the like. Such programs may be implemented in a high-level procedural or object-oriented programming language to communicate with a computer system. However, the program(s) may be implemented in assembly or machine language, if desired. In any case, the language may be a compiled or interpreted language and it may be combined with hardware implementations.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system for dispensing controlled substances and collection data associated with the controlled substances, comprising:
   a dispensing unit housing the controlled substances in respective storage compartments;
   a data collection service that receives information associated with the controlled substances;
   an application server configured to provide an interface to the information associated with the controlled substances, wherein the dispensing unit is configured to store, monitor and dispense the controlled substances as samples, wherein the dispensing unit monitors the numbers of pharmaceutical samples within respective storage compartments in the pharmaceutical dispensing unit, wherein the dispensing unit generates a prescription for a dispensed controlled substance, wherein the prescription is provided separately from the dispensed controlled substance, the prescription being used to obtain additional controlled substance at a time subsequent to the dispensing of the controlled substance and at a fulfillment site other the dispensing unit, wherein the prescription and the dispensed controlled substance are uniquely identified, wherein a filled prescription at the fulfillment site is matched to the uniquely identified prescription to create a sample/prescription pair, and wherein the sample/prescription pair is tracked to determine a return on investment (ROI), and communicates pharmaceutical samples information to a data aggregator, the pharmaceutical samples information including dispensed pharmaceutical samples, medical provider information, and generated prescriptions; and a representative device configured to access the information associated with the controlled substances through a local application running on the device, wherein the representative device is further configured to notify a representative if a number of a particular pharmaceutical sample is below a predetermined threshold or if a characteristic of the particular pharmaceutical sample reaches a second predetermined threshold.

2. The system of claim 1, further comprising an interface provide by the dispensing unit, wherein with the representative device is provided near real-time sample inventory balances within the dispensing unit.

3. The system of claim 1, further comprising an interface provide by the dispensing unit, wherein a provider device is adapted to access the interface to dispense a controlled substance.

4. The system of claim 3, wherein the provider device filters the controlled substances by one of disease state, FDA approved indications, manufacturer, product name, balances on hand for a particular controlled substance indicated for specific medical conditions.

5. The system of claim 1, further comprising an application executing on a provider device to locate a specialty physician, wherein a primary care provider electronically schedules a patient appointment with an appropriate specialty physician as determined based on symptomology.

6. The system of claim 1, further comprising an application executing on a provider device that interfaces wirelessly with at least one of clinical software that stores patient records, billing systems, the dispensing unit and the application server.

7. The system of claim 1, wherein the dispensing unit time-stamps replenishment requests, accesses to the storage compartments and identifies sample inventory by product lot number.

8. The system of claim 1, wherein a prescription is electronically transmitted to a pharmacy for fulfillment.

9. The system of claim 1, wherein the dispensing unit includes room temperature and refrigerated compartments.

10. The system of claim 1, wherein the dispensing unit prints coupons, vouchers and drug information using an associated printing device.

11. The system of claim 10, wherein the dispensing unit includes a debit card dispenser, and wherein the debit card is provided with a predetermined value to be used toward prescriptions associated with the dispensed controlled substance.

12. The system of claim 1, wherein the information associated with the controlled substances is compiled at the data collection service to derive at least one of information regarding the dispensed controlled substance as matched to generated prescriptions, patient demographics, the medical providers who dispense controlled substances that result in filled prescriptions for pharmaceuticals, representatives who provide the controlled substances to medical providers, the percentage of controlled substances that are actually dispensed to patients relative to the number of controlled substances provided by manufacturers to the representatives, and the pharmacies who receive prescriptions based on dispensed controlled substances.

13. A method for dispensing pharmaceutical samples, comprising:
   electronically receiving provider credentials at a dispensing unit;
   electronically receiving patient information at the dispensing unit;
   dispensing a sample from the dispensing unit in accordance with an authorized provider and the patient information;
   generating, by the dispensing unit, a prescription for a pharmaceutical product associated with the sample wherein the prescription is provided separately from the pharmaceutical product, the prescription being used to obtain additional pharmaceutical product at a time subsequent to the dispensing of the pharmaceutical product and at a fulfillment site other the dispensing unit;
   monitoring numbers of pharmaceutical samples within respective storage compartments in the pharmaceutical dispensing unit;
   notifying a representative if a number of a particular pharmaceutical sample is below a predetermined threshold or if a characteristic of the particular pharmaceutical sample reaches a second predetermined threshold;
   communicating sample information to a data aggregator, the pharmaceutical sample information including dispensed samples, medical provider information, and generated prescriptions;
   forwarding the sample information regarding the provider and the sample dispensed to a data collection service;
   uniquely identifying the prescription and the sample;
   matching a filled prescription at the fulfillment site to the uniquely identified prescription to create a sample/prescription pair, and
   tracking the sample/prescription to determine a return on investment (ROI).

14. The method of claim 13, further comprising sending an electronic prescription to a pharmacy or printing a hard-copy prescription.

15. The method of claim 14, further comprising:
   determining if the electronic prescription or the hard-copy prescription is filled; and
   and if so, forwarding prescription fulfillment information from a pharmacy to the data collection service.

16. The method of claim 15, further comprising:
   receiving the sample information;
   receiving prescription fulfillment information; and
   correlating the sample information with the prescription fulfillment information.

17. The method of claim 16, wherein the correlating includes at least one of determining a total number of pharmaceutical products dispensed by the dispensing unit, pharmaceutical products prescribed by medical providers, and total numbers of pharmaceutical products fulfilled by pharmacies.

18. The method of claim 16, wherein the correlating includes determining at least one of actual sample quantities being dispensed by in relation to samples manufactured, a number of generics being dispensed as substitutes for name-brand pharmaceutical products, information regarding whether name-brand or generic pharmaceutical products prescribed for which illnesses, and information regarding how pharmaceutical products are being used to create more accurate diagnostic aids.

19. A method of using a pharmaceutical dispensing unit to monitor and dispense pharmaceutical samples, comprising:
  dispensing a pharmaceutical sample from the pharmaceutical dispensing unit in accordance with instructions from a medical provider;
  generating, by the pharmaceutical dispensing unit, a prescription associated with the pharmaceutical sample that is provide separately from the pharmaceutical sample, the prescription being used to obtain additional pharmaceuticals at a time subsequent to the dispensing of the pharmaceutical sample and at a fulfillment site other the pharmaceutical dispensing unit;
  monitoring numbers of pharmaceutical samples within respective storage compartments in the pharmaceutical dispensing unit;
  notifying a representative if a number of a particular pharmaceutical sample is below a predetermined threshold or if a characteristic of the particular pharmaceutical sample reaches a second predetermined threshold;
  communicating pharmaceutical sample information to a data aggregator, the pharmaceutical sample information including dispensed pharmaceutical samples, medical provider information, and generated prescriptions;
  uniquely identifying the prescription and the sample;
  matching a filled prescription presented to the fulfillment site to the uniquely identified prescription to create a sample/prescription pair, and
  tracking the sample/prescription to determine a return on investment (ROI).

\* \* \* \* \*